United States Patent
Li et al.

[11] Patent Number: 6,129,662
[45] Date of Patent: Oct. 10, 2000

[54] SURGICAL TOOL WITH SURGICAL FIELD ILLUMINATOR

[75] Inventors: Kenneth K. Li, Arcadia; Wayne Smith, Acton; Richard B. Davies, Valencia; Douglas M. Brenner, Los Angeles, all of Calif.

[73] Assignee: Cogent Light Technologies, Inc., Santa Clara, Calif.

[21] Appl. No.: 08/657,098

[22] Filed: Jun. 3, 1996

[51] Int. Cl.[7] .................................................. A61B 1/07
[52] U.S. Cl. ....................... 600/182; 600/104; 600/176; 362/572
[58] Field of Search .................................. 600/121, 125, 600/176, 177, 182, 473, 474, 476, 478, 104, 178, 179; 362/32; 385/119, 115, 116; 604/22

[56] References Cited

U.S. PATENT DOCUMENTS

| | | |
|---|---|---|
| 3,951,514 | 4/1976 | Medina, Jr. . |
| 4,516,190 | 5/1985 | Kloots . |
| 4,666,246 | 5/1987 | Nishioka et al. ............... 600/176 |
| 4,730,885 | 3/1988 | Doi . |
| 4,757,431 | 7/1988 | Cross et al. . |
| 4,759,348 | 7/1988 | Cawood ........................ 600/126 |
| 4,782,819 | 11/1988 | Adair ............................ 600/109 |
| 4,790,295 | 12/1988 | Tashiro ......................... 600/176 |
| 4,870,952 | 10/1989 | Martinez ....................... 600/182 |
| 4,905,082 | 2/1990 | Nishigaki et al. ............. 600/109 |
| 4,986,622 | 1/1991 | Martinez ....................... 600/182 |
| 5,034,010 | 7/1991 | Kittrell et al. ................. 606/15 |
| 5,051,824 | 9/1991 | Nishigaki ...................... 600/109 |
| 5,131,380 | 7/1992 | Heller ............................ 600/121 |
| 5,190,028 | 3/1993 | Lafferty ......................... 600/176 |
| 5,197,457 | 3/1993 | Adair ............................ 600/121 |
| 5,337,734 | 8/1994 | Saab ............................. 600/121 |
| 5,337,735 | 8/1994 | Salerno ......................... 600/179 |
| 5,351,322 | 9/1994 | VonBargen .................... 385/115 |
| 5,355,285 | 10/1994 | Hicks . |
| 5,361,316 | 11/1994 | Tanaka et al. ................. 385/119 |
| 5,396,880 | 3/1995 | Kagan ........................... 600/182 |
| 5,414,600 | 5/1995 | Strobl et al. . |
| 5,423,321 | 6/1995 | Fontenot ....................... 604/22 |
| 5,430,620 | 7/1995 | Li et al. . |
| 5,446,818 | 8/1995 | Baker et al. . |
| 5,450,293 | 9/1995 | Hoffman ....................... 600/182 |
| 5,452,392 | 9/1995 | Baker et al. . |
| 5,605,532 | 2/1997 | Schermerhorn ............... 600/176 |
| 5,632,740 | 5/1997 | Koch ............................. 600/182 |
| 5,672,171 | 9/1997 | Andrus ......................... 600/108 |
| 5,681,264 | 10/1997 | Ryan ............................. 600/177 |
| 5,685,839 | 11/1997 | Edwards ....................... 604/22 |
| 5,699,795 | 12/1997 | Richards-Kortum et al. ... 600/478 |
| 5,733,241 | 3/1998 | King ............................. 600/125 |
| 5,785,645 | 4/1996 | Scheller ........................ 600/176 |

FOREIGN PATENT DOCUMENTS

| | | |
|---|---|---|
| 0082691A1 | 1/1983 | European Pat. Off. . |
| 0341919A2 | 11/1989 | European Pat. Off. . |
| 0743542 A2 | 5/1995 | European Pat. Off. ......... G02B 6/10 |
| 0743542A2 | 11/1996 | European Pat. Off. . |

*Primary Examiner*—John P. Leubecker
*Attorney, Agent, or Firm*—Rothwell, Figg, Ernst & Manbeck

[57] ABSTRACT

A surgical tool with surgical field illuminator includes a light-conveying fiber optic member having a body portion, a light-receiving end optically connectable to a source of light, and a light-delivering end. A surgical tool can be attached to, or surround, part of the body portion of the fiber optic member, and the surgical tool can be connected to the body portion of the fiber optic member. A light-transmitting member is positioned adjacent the light-delivering end of the fiber optic member. A light-delivering port in the surgical tool can be provided. When the light-receiving end of the fiber optic member is optically connected to the source of light, light is transmitted through the fiber optic member to the light-delivering end of the fiber optic member, and through the light-transmitting member at a light density, to illuminate a surgical region adjacent the light-transmitting member.

40 Claims, 3 Drawing Sheets

SURGICAL TOOL WITH SURGICAL FIELD ILLUMINATOR

BACKGROUND OF THE INVENTION

1. Field of the Invention

The present invention relates to the fields of surgical tools and surgical field illuminators.

2. Description of the Background Art

Fiber optic technology has facilitated the development of various surgical illumination systems. Such systems can utilize bundles of fiber optic filaments to transmit light. Alternatively, light can be transmitted utilizing a single fiber optic filament in light-weight systems.

An example of a surgical headlamp utilizing a fiber optic cable, i.e., a bundle of fiber optic filaments, is shown in U.S. Pat. No. 4,516,190 to Kloots.

U.S. Pat. No. 5,430,620 to Li et al., assigned to the Assignee of the present invention, discloses a compact surgical headlamp utilizing a single core fiber optic delivery lightguide, in a particularly light-weight system.

U.S. Pat. No. 4,870,952 discloses a single filament fiber optic illuminator for use in ophthalmic surgery to direct light to various parts of the eye. The device includes a rigid cannula to be held by a surgeon, through which extends a fiber optic element, terminating a distal end of the rigid cannula, to direct light out the end of the cannula and into a patient's eye.

Although various surgical illuminators are disclosed in the patents discussed above, and other illuminated surgical tools can be found in the market, none both combines a surgical tool with a fiber optic light-conveying member, and provides the features necessary to deliver high-intensity light without creating tissue desiccation and damage.

There remains a need in the art for a combination surgical tool with high-intensity surgical field illumination.

SUMMARY OF THE INVENTION

In accordance with the present invention, a surgical tool with surgical field illuminator comprises a light-conveying fiber optic member having a body portion, a light-receiving end optically connectable to a source of light, and a light-delivering end. A surgical tool is connectable to the fiber optic member. A light-transmitting member is positioned adjacent the light-delivering end of the fiber optic member. When the light-receiving end of the fiber optic member is optically connected to the source of light, light is transmitted through the fiber optic member to the light-delivering end of the fiber optic member, and through the light-transmitting member at a light density, so as to illuminate an adjacent surgical region.

DETAILED DESCRIPTION OF THE PREFERRED EMBODIMENTS

Figure 1:
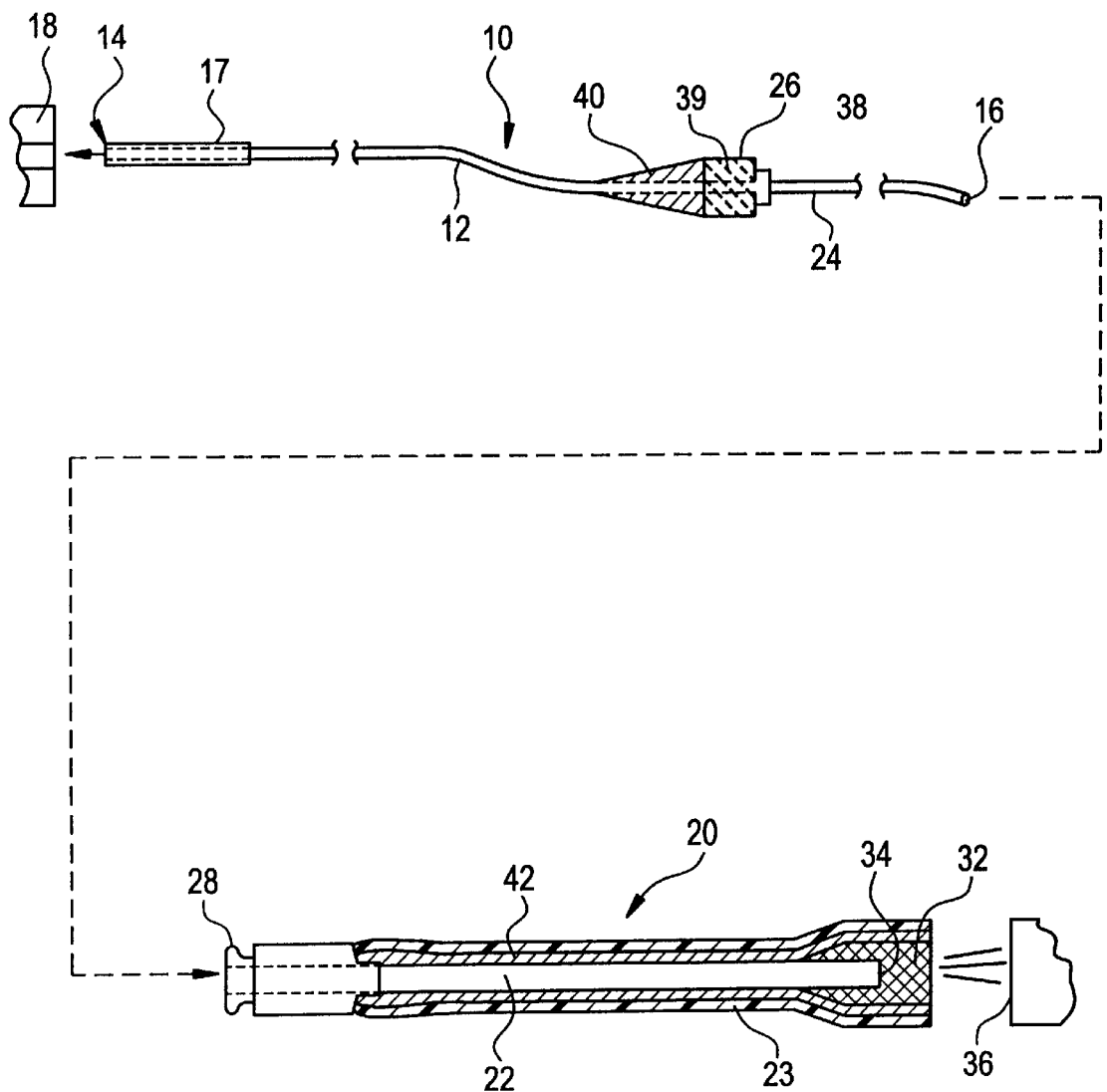
FIG. 1 is a partially-exploded elevational view, somewhat schematic, of a surgical tool with surgical field illuminator in accordance with one embodiment of the invention.

With reference to FIG. 1, a surgical tool with surgical field illuminator in accordance with one embodiment of the present invention includes a light-conveying fiber optic member 10 having a body portion 12, a light-receiving end 14 and a light-delivering end 16.

Adjacent the light-receiving end 14 of fiber optic member 10 is a connector 17 which may be formed of any suitable material, such as stainless steel tubing.

The light-receiving end 14 of fiber optic member 10 is optically connectable to a source of light 18.

The present invention may include a surgical tool such as a micro-retractor cannula 20. Cannula 20 includes a malleable stainless steel tube 22. When the surgical tool 20 is a micro-retractor cannula as shown in FIG. 1, the cannula advantageously has a length within the range of from about 4–8 inches, more preferably about 6 inches.

Tube 22 preferably has an outer diameter of about 1.5–3 mm, more preferably about 2 mm, and an inner diameter of about 1–2 mm, more preferably about 1.2 mm.

When assembled, stainless steel tube 22 of cannula 20 can surround a part 24 of the body portion 12 of fiber optic member 10 adjacent the light-delivering end 16 of fiber optic member 10. The stainless steel tube 22 may be surrounded by a polymeric sheath 23 of heat shrinking material. In accordance with this embodiment, a connector is provided for connecting the fiber optic member 10 with a surgical tool 20 such as shown in FIG. 1. In accordance with this embodiment, the connector is comprised of a Luer lock member 26 which mates with corresponding Luer lock member 28. In accordance with this embodiment, connector member 26 is connected to an intermediate section 30 of the body portion 12 of fiber optic member 10 spaced away from the light-delivering end 16. A tool-insertable section 24 of fiber optic member 12 extends between connector member 26 and the light-delivering end 16 of fiber optic member 12. When the light-delivering end 16 of fiber optic member 12 and the tool-insertable section 24 thereof is received within the surgical tool 20, Luer lock connector member 28 thereof is mated with Luer lock connector member 26. In accordance with this embodiment, connector members 26 and 28 provide a releasable connection between the fiber optic member 12 and surgical tool 20, so as to releasably attach tool 20 to fiber optic member 12.

In this embodiment, fiber optic member 12 is positioned in a corresponding opening 38 through connector member 26. Luer lock member 26 is fixedly connected to an intermediate section 30 of the body portion 12 of fiber optic member 10 by any suitable means, such as epoxy adhesive. Similarly, Luer lock member 28 can be fixedly connected to the malleable stainless steel tube 22 of cannula 20 by any suitable means, such as press-fitting, epoxy adhesive and the like.

Figure 3:
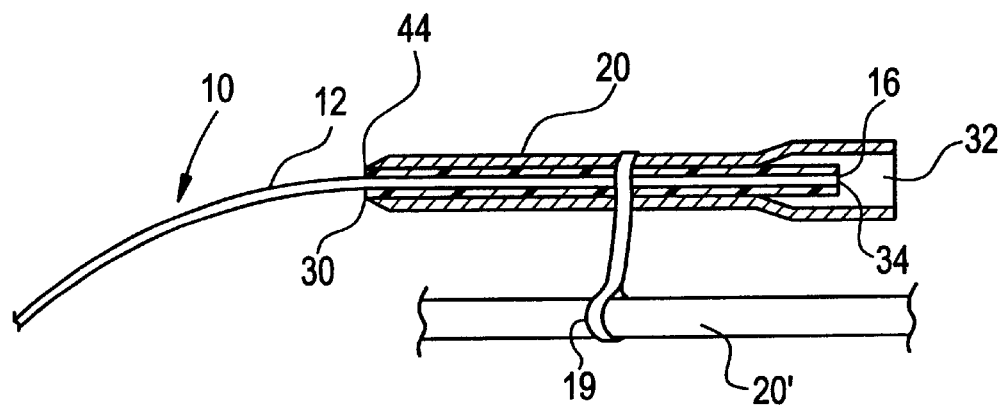
FIG. 3 is an elevational view, somewhat schematic and in partial cross-section, of a portion of a surgical tool with surgical field illuminator in accordance with another embodiment.

In accordance with another embodiment, a surgical tool 20 is fixedly connected to an intermediate section 30 of the body portion 12 of the fiber optic member by any suitable means, such as by epoxy adhesive 44 as shown in FIG. 3.

In the embodiment shown in FIG. 1, a light-transmitting member 32 is provided adjacent a light-delivering port 34 in surgical tool 20. Member 32 is at the end of stainless steel tubing 22 opposite Luer lock member 28. When assembled, the light-transmitting member 32 is positioned adjacent the light-delivering end 16 of the fiber optic member 10.

In the embodiment shown in FIG. 1, the light-transmitting member 32 is attached to port 34 of stainless steel tubing 22 of tool 20 by any suitable means, such as epoxy adhesive, press-fitting, etc.

Figure 2:
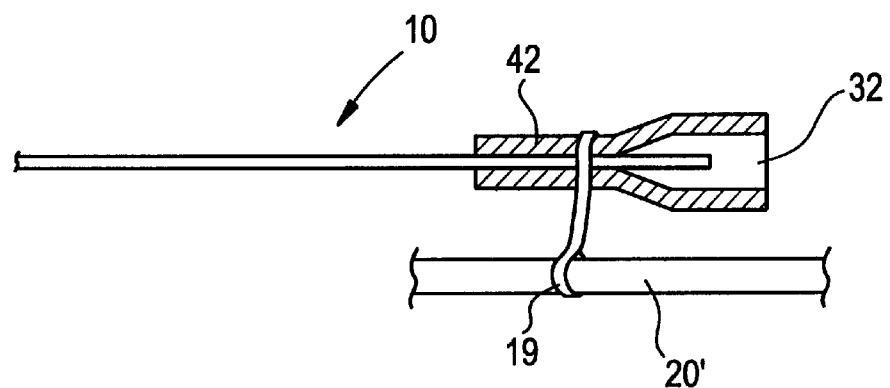
FIG. 2 is an elevational view, somewhat schematic and in partial cross-section, of a surgical field illuminator in accordance with a second embodiment.

In alternative embodiments, the light-transmitting member 32 can be attached directly to the fiber optic member 10 as shown in FIG. 2, and include an external heat-shrink polymeric tubing 42. In accordance with this embodiment, the fiber optic member 10 and the light-transmitting member 32 can both be insertable into a corresponding surgical tool 20. Alternatively, fiber optic member 10 attached to light-transmitting member 32 are externally attachable (by any suitable attachment member 19 such as a clip, tape or the like) to a nonilluminated surgical tool 20' such as a suction or suction-irrigation cannula, retractor, electrocautery device, and the like.

In preferred embodiments, the light-transmitting member is a window of light-transmitting material having a thickness sufficient to reduce the light density transmitted through window 32 and out port 34 of surgical tool 20 so that a surface temperature of adjacent surgical region 36 rises less than about 55° C. when light is transmitted through window 32 to region 36. In preferred embodiments, window 32 is about 2–6 mm in thickness, and more preferably about 4 mm in thickness. The light-transmitting member can be formed of a plastic, glass or the like. Suitable plastics include acrylic plastics such as PMMA (polymethylmethacrylate), polycarbonate plastics, and the like. Suitable glass materials include borosilicate glass such as BK 7, silica (quartz) glass, and the like.

FIG. 3 shows an embodiment where the light-transmitting member 32 is a window of light-transmitting material, the window being spaced away from the light-delivering end 16 of the fiber optic member 10 by a distance greater than about 0.001 inch and less than about 0.1 inch, so that light transmitted out port 34 and through window 32 raises the surface temperature of an adjacent surgical region less than about 55° C. when light is transmitted through window 32 to the region.

In preferred embodiments, a proximal strain-relieving member 40 formed of flexible rubber-like material is provided proximal to Luer lock connector member 26.

When assembled, and when the light-receiving end 14 of the fiber optic member 12 is optically connected to the source of light 18, light is transmitted through the fiber optic member 10 to the light-delivering end 16 of the fiber optic member 10, out the port 34 of the surgical tool, and through the light-transmitting member 32, so as to illuminate a surgical region 36 adjacent the light-transmitting member 32.

In preferred embodiments wherein surgical tool 20 is a micro-retractor cannula, the malleable stainless steel tubing 22 is covered on its outer surface with medical grade heat-shrink polymeric tubing 42.

Figure 4:
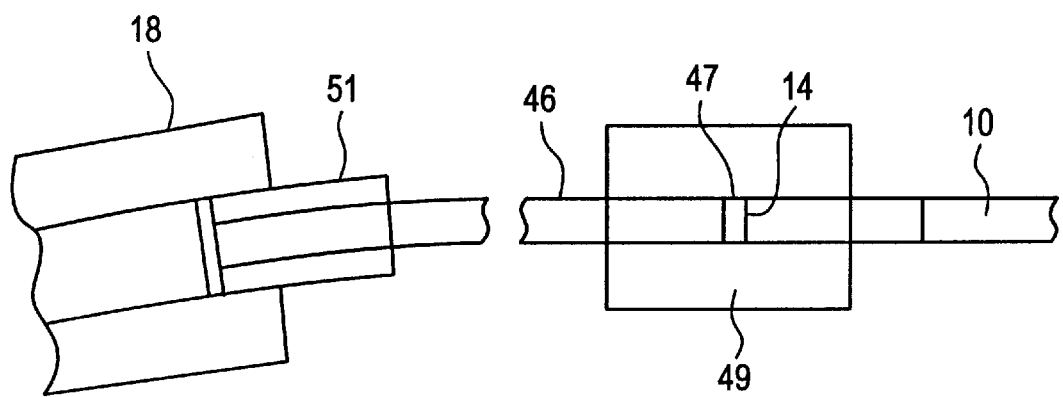
FIG. 4 is a schematic view in partial cross-section showing a light-conveying member for use with the present invention.

In a further embodiment shown in FIG. 4, a second light-conveying member 46 is provided, positioned between the light-receiving end 14 and the source of light 18, for optically connecting the light-receiving end 14 with source of light 18. In the embodiment shown in FIG. 4, the light-delivering end 47 of the second light-conveying member 46 is spaced apart from the light-receiving end 14 of fiber optic member 10. In preferred embodiments, the light-delivering end 47 of the second fiber optic member 46 is spaced apart from the light-receiving end 14 a distance greater than about 0.01 inch and less than about 0.1 inch. For example, with a 2 Watt output of visible light from a 0.47 mm diameter quartz fiber, the spacing between the quartz fiber and a 1.0 mm diameter acrylic fiber optic should approximate 0.07 inch, corresponding to about 18% coupling efficiency, so as to minimize potential damage to the acrylic fiber. This embodiment can utilize a fiber optic connector 49 such as is disclosed in commonly-owned U.S. Pat. No. 5,446,818, incorporated herein by reference, with or without a fiber optic coupler 51 as disclosed in commonly-owned U.S. Pat. No. 5,452,392, also incorporated herein by reference.

In accordance with a preferred embodiment, the fiber optic member 10 is a single fiber optic filament having a diameter of from about 0.1–2 mm, preferably about 1 mm and most preferably is formed of a flexible plastic material, preferably acrylic.

Figure 5:
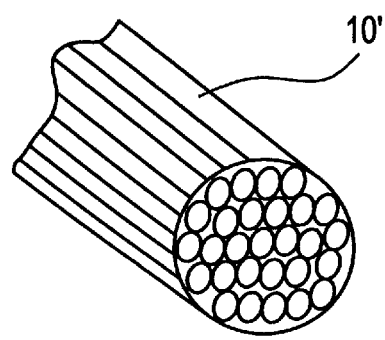
FIG. 5 is a perspective view, somewhat schematic and in partial cross-section, of a fiber optic bundle for use in accordance with one embodiment of the invention.

In other embodiments, the light-conveying fiber optic member 10 is a bundle 10' of optical fibers, as shown in FIG. 5.

The invention also may utilize surgical tools other than a micro-retractor cannula, including surgical suction or suction-irrigation cannulae, electrocautery devices, non-malleable retractors, and power tools. In addition, a surgical tool in accordance with the present invention may itself be attached to other non-illuminated surgical tools 20' by a suitable attachment member 19 (see FIG. 3). Suitable surgical tools 20' are exemplified above, and in accordance with this embodiment, provide illuminated surgical devices as exemplified in FIG. 3.

The present invention can provide a lighted device which also may be malleable, such that the illumination can be directed to a desired position by the surgeon during a surgical procedure. At the same time, the malleable end can also be used as a retractor. In addition, by minimizing the potential for thermal damage to tissue, such malleable lighted retractors can be used for trans-illumination of tissue during retraction.

The present invention provides several advantages over other types of lighted retractors, as such typically are fixed in configuration and cannot be modified in shape during a surgical procedure.

The invention also provides embodiments in which the tool 20 can be disposable and easily replaced utilizing a Luer lock connecting member.

Additional advantages of the single fiber embodiment are low cost, versatility, and single fiber flexibility and convenience, avoiding the bulkiness and potential added fragility of a fiber optic bundle.

Because many modifications, variations and changes in detail may be made to the described embodiments, it is intended that matter in the foregoing description and shown in the accompanying drawings be interpreted as illustrative and not in a limiting sense.

What is claimed is:

1. A surgical tool with surgical field illuminator, comprising:
   a) a light-conveying fiber optic member having a body portion, a light-receiving end optically connectable to a source of light, and a light-delivering end;
   b) a rigid, elongated surgical tool surrounding part of the body portion of said fiber optic member adjacent the light-delivering end of said fiber optic member, wherein said surgical tool is releasably connected to said body portion of said fiber optic member;

c) a light-transmitting member positioned adjacent the light-delivering end of said fiber optic member; and d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; wherein said surgical tool is fixedly connected to an intermediate section of said body portion of said fiber optic member.

2. The surgical tool of claim 1, wherein said light-transmitting member is attached to said port of said surgical tool.

3. The surgical tool of claim 1, wherein said light-transmitting member is a window of light-transmitting material having a thickness sufficient to reduce the light density transmitted out said port of said surgical tool and through said window so that a surface temperature of said adjacent surgical region rises less than about 55° C. when light is transmitted through said window to said region.

4. The surgical tool of claim 3, wherein said window is about 4 mm in thickness.

5. The surgical tool of claim 1, wherein said tool is comprised of a malleable stainless steel tube, and further comprising a polymeric sheath of heat-shrinking material surrounding said malleable stainless steel tube.

6. The surgical tool of claim 2, wherein said surgical tool is a cannula having a length of between about 4 to 8 inches.

7. The surgical tool of claim 6, wherein said cannula has an outer diameter of between about 1½ to 3 mm.

8. The surgical tool of claim 7, wherein said cannula has an inner diameter of between about 1 to 2 mm.

9. The surgical tool of claim 1, wherein said surgical tool is made from a material that is malleable such that the cannula can be bent to a desired position.

10. A surgical tool with surgical field illuminator, comprising:

a) a light-conveying fiber optic member having a body portion, a light-receiving end optically connectable to a source of light, and a light-delivering end;

b) a rigid, elongated surgical tool surrounding part of the body portion of said fiber optic member adjacent the light-delivering end of said fiber optic member, wherein said surgical tool is releasably connected to said body portion of said fiber optic member;

c) a light-transmitting member positioned adjacent the light-delivering end of said fiber optic member; and d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; further comprising a connector for connecting said fiber optic member with said surgical tool, said connector being connected to an intermediate section of the body portion of said fiber optic member spaced away from said light-delivering end, so that a tool-insertable section of said fiber optic member extends between said connector and the light-delivering end of said fiber optic member, wherein the light-delivering end of said fiber optic member and said tool-insertable section of said fiber optic member is received within said surgical tool when said surgical tool is connected to said connector.

11. The surgical tool of claim 10, wherein said connector provides a releasable connection between said fiber optic member and said surgical tool.

12. The surgical tool of claim 10, wherein said fiber optic member is positioned in a corresponding opening through said connector, and said connector is attached to said intermediate section of the body portion of said fiber optic member.

13. The surgical tool of claim 12, wherein said tool has a corresponding connector member which is joinable with the connector attached to said fiber optic member, so as to attach said tool to said fiber optic member.

14. A surgical tool with surgical field illuminator, comprising:

a) a light-conveying fiber optic member having a body portion, a light-receiving end optically connectable to a source of light, and a light-delivering end;

b) a surgical tool surrounding part of the body portion of said fiber optic member adjacent the light-delivering end of said fiber optic member, wherein said surgical tool is connected to said body portion of said fiber optic member;

c) a light-transmitting member positioned adjacent the light-delivering end of said fiber optic member; and d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, so as to illuminate a surgical region adjacent said light-transmitting member;

wherein said fiber optic member is a single fiber having a diameter of from about 0.1–2 mm.

15. The surgical tool of claim 14, wherein said fiber is formed of a plastic material.

16. The surgical tool of claim 15, wherein said fiber is flexible.

17. A surgical tool with surgical field illuminator, comprising:

a) a light-conveying fiber optic member having a body portion, a light-receiving end optically connectable to a source of light, and a light-delivering end;

b) a rigid, elongated surgical tool surrounding part of the body portion of said fiber optic member adjacent the light-delivering end of said fiber optic member, wherein said surgical tool is releasably connected to said body portion of said fiber optic member;

c) a light-transmitting member positioned adjacent the light-delivering end of said fiber optic member; and d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; wherein said light-transmitting member is attached to said fiber optic member.

18. The surgical tool of claim 17, wherein said fiber optic member and said light-transmitting member are both insertable into said surgical tool.

19. A surgical tool with surgical field illuminator, comprising:
   a) a light-conveying fiber optic member having a body portion, a light-receiving end optically connectable to a source of light, and a light-delivering end;
   b) a rigid, elongated surgical tool surrounding part of the body portion of said fiber optic member adjacent the light-delivering end of said fiber optic member, wherein said surgical tool is releasably connected to said body portion of said fiber optic member;
   c) a light-transmitting member positioned adjacent the light-delivering end of said fiber optic member; and
   d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; further comprising a second light-conveying fiber optic member positioned between said light-receiving end and said source of light, and spaced apart from said light-receiving end, for optically connecting said light-receiving end with said source of light.

20. The surgical tool of claim 19, further including a stainless steel tube surrounding said light-receiving end and at least a portion of said second fiber optic member.

21. A surgical tool with surgical field illuminator, comprising:
   a) a light-conveying fiber optic member having a body portion, a light-receiving end optically connectable to a source of light, and a light-delivering end;
   b) a surgical tool surrounding part of the body portion of said fiber optic member adjacent the light-delivering end of said fiber optic member, wherein said surgical tool is connected to said body portion of said fiber optic member;
   c) a light-transmitting member positioned adjacent the light-delivering end of said fiber optic member; and
   d) a light-delivering port in said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, so as to illuminate a surgical region adjacent said light-transmitting member:
      further comprising a second light-conveying fiber optic member positioned between said light-receiving end and said source of light, and spaced apart from said light-receiving end, for optically connecting said light-receiving end with said source of light; and
      wherein said second fiber optic member is spaced apart from said light-receiving end a distance greater than about 0.01 inch and less than about 0.1 inch.

22. The surgical tool of claim 21, wherein said second fiber optic member is spaced apart from said light-receiving end a distance of about 0.07 inch.

23. A surgical tool with surgical field illuminator, comprising:
   a) a light-conveying fiber optic member having a body portion, a light-receiving end optically connectable to a source of light, and a light-delivering end;
   b) a rigid, elongated surgical tool surrounding part of the body portion of said fiber optic member adjacent the light-delivering end of said fiber optic member, wherein said surgical tool is releasably connected to said body portion of said fiber optic member;
   c) a light-transmitting member positioned adjacent the light-delivering end of said fiber optic member; and
   d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; wherein said light-transmitting member is a window of light-transmitting material, said window being spaced away from the light-delivering end of said fiber optic member so that light transmitted through said window and out said port of said surgical tool raises the surface temperature of said adjacent surgical region less than about 55° C. when light is transmitted through said window to said region.

24. A surgical tool with surgical field illuminator, comprising:
   a) a light-conveying fiber optic member having a body portion, a light-receiving end optically connectable to a source of light, and a light-delivering end;
   b) a rigid, elongated surgical tool surrounding part of the body portion of said fiber optic member adjacent the light-delivering end of said fiber optic member, wherein said surgical tool is releasably connected to said body portion of said fiber optic member;
   c) a light-transmitting member positioned adjacent the light-delivering end of said fiber optic member; and
   d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, said light-delivering end being adjacent said light-transmitting member so as to illuminate a surgical region adjacent said light-transmitting member; further including an attachment member for attaching said surgical tool to another surgical tool.

25. A surgical tool with surgical field illuminator, comprising:
   a light-conveying fiber optic member having a body portion, a light-receiving end optically connectable to a source of light, and a light-delivering end;
   a light-transmitting member positioned adjacent the light-delivering end of said fiber optic member and attached to said fiber optic member, wherein, when said light-receiving end of said fiber optic member is optically connected to said source of light, light is transmitted through said fiber optic member to said light-delivering end of said fiber optic member, through said light-transmitting member at a light density, so as to illuminate a surgical region adjacent said light-transmitting member, the light-transmitting member and light-conveying fiber optic member together forming a light-conveying assembly; and an attachment member for attaching the light-conveying assembly laterally displaced from but generally parallel to an elongated surgical tool so as to provide an illuminated surgical device with illumination for said surgical tool.

26. A surgical tool with surgical field illuminator, comprising:
a) a light-conveying bundle of optical fibers having a body portion, a light-receiving end optically connectable to a source of light, and a light-delivering end;
b) a rigid, elongated surgical tool surrounding part of the body portion of said bundle adjacent the light-delivering end of said bundle;
c) a connector for connecting said bundle with said surgical tool, said connector being releasably connected to an intermediate section of the body portion of said bundle spaced away from said light-delivering end, so that a tool-insertable section of said bundle extends between said connector and the light-delivering end of said bundle, wherein the light-delivering end of said bundle and said tool-insertable section of said bundle is received within said surgical tool when said surgical tool is connected to said connector;
d) a light-transmitting member positioned adjacent the light-delivering end of said bundle; and
e) said light-delivering end of said bundle being positioned adjacent a light-delivering port formed as an opening through a distal endface of said surgical tool, so that when said light-receiving end of said bundle is optically connected to said source of light, light is transmitted through said bundle to said light-delivering end of said bundle, out said port of said surgical tool and through said light-transmitting member at a light density, so as to illuminate a surgical region adjacent said light-transmitting member.

27. The surgical tool of claim 26, wherein said light-transmitting member is attached to said port of said surgical tool.

28. The surgical tool of claim 26, wherein said light-transmitting member is attached to said bundle.

29. The surgical tool of claim 26, wherein said light-transmitting member is a window of light-transmitting material having a thickness sufficient to reduce the light density transmitted out said port of said surgical tool and through said window so that the surface temperature of said adjacent surgical region rises less than about 55° C. when light is transmitted through said window to said region.

30. The surgical tool of claim 26, wherein said light-transmitting member is a window of light-transmitting material, said window being spaced away from the light-delivering end of said fiber optic member so that light transmitted out said port of said surgical tool, and through said window, raises the surface temperature of said adjacent surgical region less than about 55° C. when light is transmitted through said window to said region.

31. The surgical tool of claim 26, further including an attachment member for attaching said surgical tool to another surgical tool.

32. The surgical tool of claim 26, wherein said surgical tool is a cannula having a length of between about 4 to 8 inches.

33. The surgical tool of claim 32, wherein said cannula has an outer diameter of between about 1½ to 3 mm.

34. The surgical tool of claim 33, wherein said cannula has an inner diameter of between about 1 to 2 mm.

35. The surgical tool of claim 26, wherein said surgical tool is made from a material that is malleable such that the cannula can be bent to a desired position.

36. A surgical tool with surgical field illuminator, comprising:
a) a light-conveying fiber optic member having a body portion, a light-receiving end optically connectable to a source of light, and a light-delivering end;
b) a rigid surgical tool surrounding part of the body portion of said fiber optic member adjacent the light-delivering end of said fiber optic member, wherein said surgical tool is releasably connected to said body portion of said fiber optic member;
c) a light-transmitting member positioned adjacent the light-delivering end of said fiber optic member;
d) a light-delivering port formed as an opening through a distal endface of said surgical tool, wherein, when said light-receiving end of said fiber optic member is optically connected to said source of light, light is transmitted through said fiber optic member to said light-delivering end of said fiber optic member, out said port of said surgical tool and through said light-transmitting member at a light density, so as to illuminate a surgical region adjacent said light-transmitting member;
e) wherein said fiber optic member is a single fiber that is readily flexed to an interior configuration of said tool; whereby said single fiber is connectable to said tool for use and releasable from said tool for disposal or replacement.

37. The surgical tool of claim 36, wherein said single fiber has a diameter of from about 0.1–2 mm.

38. The surgical tool of claim 36, wherein said surgical tool is releasably connected to said body portion of said fiber optic member via a Leur lock connector.

39. The surgical tool of claim 38, further including a strain-relieving member formed of flexible material provided proximal to the Luer lock connector.

40. The surgical tool of claim 34, wherein said single fiber is inserted within said tool in such a manner as to be bend around a longitudinal axis of said fiber.

* * * * *